United States Patent
Marquez

(10) Patent No.: US 7,063,722 B2
(45) Date of Patent: Jun. 20, 2006

(54) METHOD OF IMPLANTING A SELF-MOLDING ANNULOPLASTY RING

(75) Inventor: Salvador Marquez, Foothill Ranch, CA (US)

(73) Assignee: Edwards Lifesciences, LLC, Irvine, CA (US)

(*) Notice: Subject to any disclaimer, the term of this patent is extended or adjusted under 35 U.S.C. 154(b) by 0 days.

(21) Appl. No.: 10/777,343

(22) Filed: Feb. 12, 2004

(65) Prior Publication Data

US 2004/0162611 A1 Aug. 19, 2004

Related U.S. Application Data

(63) Continuation of application No. 09/938,902, filed on Aug. 24, 2001, now Pat. No. 6,726,716.

(51) Int. Cl.
*A61F 2/24* (2006.01)

(52) U.S. Cl. ............ 623/2.36; 623/2.37; 623/902

(58) Field of Classification Search ............ 623/2.36, 623/2.37, 2.11, 902
See application file for complete search history.

(56) References Cited

U.S. PATENT DOCUMENTS

| | | | |
|---|---|---|---|
| 4,042,979 A | 8/1977 | Angell | |
| 4,290,151 A | 9/1981 | Massana | |
| 4,489,446 A | 12/1984 | Reed | |
| 4,602,911 A | 7/1986 | Ahmadi et al. | |
| 4,917,698 A | 4/1990 | Carpentier et al. | |
| 5,064,431 A | 11/1991 | Gilbertson et al. | |
| 5,163,953 A | 11/1992 | Vince | |
| 5,201,880 A * | 4/1993 | Wright et al. ............ | 623/2.37 |
| 5,450,860 A | 9/1995 | O'Connor | |
| 5,474,557 A * | 12/1995 | Mai ............ | 606/78 |
| 5,593,424 A | 1/1997 | Northrup, III | |
| 5,593,435 A | 1/1997 | Carpentier et al. | |
| 5,607,471 A | 3/1997 | Sequin et al. | |
| 5,716,397 A | 2/1998 | Myers | |
| 5,824,066 A | 10/1998 | Gross | |
| 5,843,178 A | 12/1998 | Vanney et al. | |
| 5,855,601 A | 1/1999 | Bessler et al. | |
| 5,895,419 A * | 4/1999 | Tweden et al. ............ | 623/2.36 |
| 6,019,791 A | 2/2000 | Wood | |

(Continued)

FOREIGN PATENT DOCUMENTS

FR 2 708 458 2/1995

(Continued)

OTHER PUBLICATIONS

Melo et al., "Atrioventricular Valve Repair Using Externally Adjustable Flexible Rings", The Journal of Thoracic Cardiovascular Surgery, vol. 110, No. 5, 1995.*

(Continued)

*Primary Examiner*—Paul B. Prebilic
(74) *Attorney, Agent, or Firm*—Guy Cumberbatch; Debra D. Condino

(57) ABSTRACT

A method of implanting a resilient self-molding annuloplasty ring including stretching it to an expanded diameter and attaching it to a heart valve annulus, then permitting the ring to contract to reduce the diameter of the annulus. The ring may be positioned on an insertion device that maintains the ring in its expanded diameter while attaching to the annulus. The resilient self molding annuloplasty ring which may be enlarged prior to implantation to facilitate implantation within a dilated or otherwise incompetent valve annulus having sufficient contractive force to render a valve competent. The self molding annuloplasty ring of the invention may further comprise integral attachment devices to aid in the implantation process.

41 Claims, 7 Drawing Sheets

U.S. PATENT DOCUMENTS

| | | | |
|---|---|---|---|
| 6,183,512 B1 | 2/2001 | Howanec, Jr. et al. | |
| 6,187,040 B1 | 2/2001 | Wright | |
| 6,210,432 B1 | 4/2001 | Solem et al. | |
| 6,217,610 B1 | 4/2001 | Carpentier et al. | |
| 6,283,993 B1* | 9/2001 | Cosgrove et al. | 623/2.11 |
| 6,402,781 B1 | 6/2002 | Langberg et al. | |
| 6,416,549 B1 | 7/2002 | Chinn et al. | |
| 6,419,696 B1* | 7/2002 | Ortiz et al. | 623/2.37 |
| 6,702,826 B1* | 3/2004 | Liddicoat et al. | 606/151 |
| 6,726,716 B1* | 4/2004 | Marquez | 623/2.36 |
| 2001/0049558 A1 | 12/2001 | Liddicoat et al. | |
| 2002/0002401 A1* | 1/2002 | McGuckin et al. | 623/1.19 |
| 2002/0032480 A1* | 3/2002 | Spence et al. | 623/2.11 |
| 2002/0042621 A1* | 4/2002 | Liddicoat et al. | 606/151 |
| 2002/0099439 A1* | 7/2002 | Schwartz et al. | 623/1.24 |
| 2003/0199974 A1* | 10/2003 | Lee et al. | 623/2.36 |
| 2004/0102840 A1* | 5/2004 | Solem et al. | 623/2.11 |
| 2004/0243230 A1* | 12/2004 | Navia et al. | 623/2.36 |

FOREIGN PATENT DOCUMENTS

| | | |
|---|---|---|
| SU | 0577022 * | 10/1977 |
| WO | WO 90/09153 | 8/1990 |
| WO | WO 91/17721 A1 | 11/1991 |
| WO | WO 01/06935 | 2/2001 |

OTHER PUBLICATIONS

U.S. Appl. No. 60/236,501 by Schwatz et al filed Sep. 29, 2000.*

* cited by examiner

METHOD OF IMPLANTING A SELF-MOLDING ANNULOPLASTY RING

RELATED APPLICATIONS

The present application is a continuation of Ser. No. 09/938,902, filed Aug. 24, 2001, now U.S. Pat. No. 6,726,716 entitled SELF-MOLDING ANNULOPLASTY RING, which application is expressly incorporated herein by reference.

BACKGROUND OF THE INVENTION

The human heart is hollow muscular organ having four pumping chambers separated by four heart valves. The mitral and tricuspid valves, present at the left and right atrio-ventricular junctions, open and close in response to a pressure gradient during each cardiac cycle of relaxation and contraction to control the flow of blood to a particular region of the heart These valves are comprised of a dense fibrous ring known as the annulus, leaflets or cusps attached to the annulus, and a complex of chordae tendineae and papillary muscles securing the leaflets. The size of the leaflets or cusps is such that when the heart contracts the resulting increased blood pressure formed within the ventricular cavity forces the leaflets towards the arterial cavity. As a result, the leaflets or cusps come in apposition to each other thereby closing the atrio-ventricular passage.

Natural defects and heart disease are common causes of valvular dysfunction within the heart of a patient. One common example of valvular dysfunction occurs when the annulus becomes excessively dilated or the valve geometry results in ineffective valve closure, which results in regurgitation. Due to the increased diameter of the annulus, the leaflets or cusps fail to meet during systolic contraction, thereby resulting in the regurgitation of blood during ventricular contractions. As such, sufficient back pressure exists within the chambers of the heart capable of forcing some blood flow to traverse the atrio-ventricular junction from the ventricle to the atria.

One manner of repairing this problem involves surgically implanting a prosthetic ring (i.e. "annuloplasty ring") about the dilated annulus, thereby restoring the annulus to the normal size and shape and allowing the valve leaflets to function normally. Commonly, a surgeon positions the annuloplasty ring near the valve annulus and sutures the device in place.

One approach to correcting or remodeling the valve annulus has required the implantation of a rigid annuloplasty ring. Typically, an annuloplasty ring having the desired internal diameter is positioned near the heart valve and sutured in place. As a result, the diameter of the valve is reduced to the diameter of the annuloplasty ring. This procedure utilizing current annuloplasty rings has several shortcomings. For example, the tissue comprising the heart, particularly in the area of the heart valves, is flexible. The implantation of a rigid annuloplasty ring restricts the natural flexibility of this tissue, and may impact the heart's function. Also, the diameter of the dilated annulus is substantially larger than the annuloplasty ring, thereby making the implantation surgery unnecessarily time consuming. The surgeon is required to position the prosthesis near a portion of the tissue and suture the ring in place. Thereafter, the opposing tissue is forced to engage the ring and is attached to the annuloplasty ring with sutures. Consequently, the sutures may be under different stress loads, and could result in an increased risk of ring dehiscence.

There is thus a need for a flexible annuloplasty prosthesis and implantation device which enables a surgeon to precisely position and apply an annuloplasty ring to the dilated valve annulus.

SUMMARY OF THE INVENTION

The present invention solves the aforementioned problems in that the resilient annuloplasty ring of the present invention may be stretched to the diameter of the dilated valve annulus prior to implantation, thereby simplifying the implantation process. In addition, the contractive force of the resilient annuloplasty ring of the present invention may controllably reduce the diameter of an incompetent dilated valve annulus to more competent diameter. Those skilled in the art will appreciate the present invention is easy to manufacture and may be manufactured from a plurality of materials.

The annuloplasty ring of the present invention comprises a resilient inner sizing member positioned within a flexible outer attachment sheath. The resilient inner sizing member applies a contractive force to the incompetent annulus tissue. The flexible outer attachment sheath permits the surgeon to attach the device to the annulus tissue in a plurality of manners including suturing and stapling. The annuloplasty ring of the present invention may be manufactured from a plurality of biologically compatible materials having sufficient resiliency to permit stretching during implantation and having sufficient contractive force to permit a reduction in the diameter of the incompetent valve annulus.

An alternate embodiment of the present self molding annuloplasty ring comprises an resilient inner sizing member positioned within a flexible outer attachment sheath, the ring further having a plurality of attachment members positioned thereon. The attachment members may comprise a plurality of devices, including, without limitation, needles, barbs, or hooks. In addition, the attachment members may be manufactured from a biologically compatible material such as, without limitation, stainless steel, titanium, and Nitinol.

In yet another embodiment of the present invention, a self molding annuloplasty ring having a predetermined contracted diameter is disclosed. This embodiment comprises a resilient inner sizing member positioned within a series of individual support members. A flexible outer attachment sheath is positioned on the exterior of the support members. This embodiment permits the surgeon to predetermine the inner diameter of a repaired valve annulus, thereby rendering an incompetent valve competent. Those skilled in the art will appreciate that the support members may be manufactured from a biologically compatible material such as, without limitation, plastic and elastomer.

Other objects, features, and advantages of the present invention will become apparent from a consideration of the following description of the preferred embodiments.

BRIEF DESCRIPTION OF THE DRAWINGS

The apparatus of the present invention will be explained in more detail by way of the accompanying drawings, wherein.

DESCRIPTION OF THE PREFERRED EMBODIMENTS

The following detailed description and the accompanying drawings are intended to describe and show certain presently preferred embodiments of the present invention, and are not intended to limit the scope of the invention in any way.

The self-molding annuloplasty ring of the present invention is generally used in surgical procedures to repair an incompetent tissue annulus. More specifically, the present invention is used to render an otherwise incompetent heart valve competent by decreasing the diameter of the opening at the valvular junction. As those skilled in the art will appreciate, the present invention may be manufactured with varying degrees of pre-tension and contractive force, thereby permitting variations of the contraction of the anterior and/or posterior annuli. In addition, the present invention simplifies the implantation procedure by permitting pre-stretching of the annuloplasty ring to the diameter of the dilated annulus, and thereafter reducing the annulus with the contractive force exerted by the self-molding annulus ring.

Figure 1:
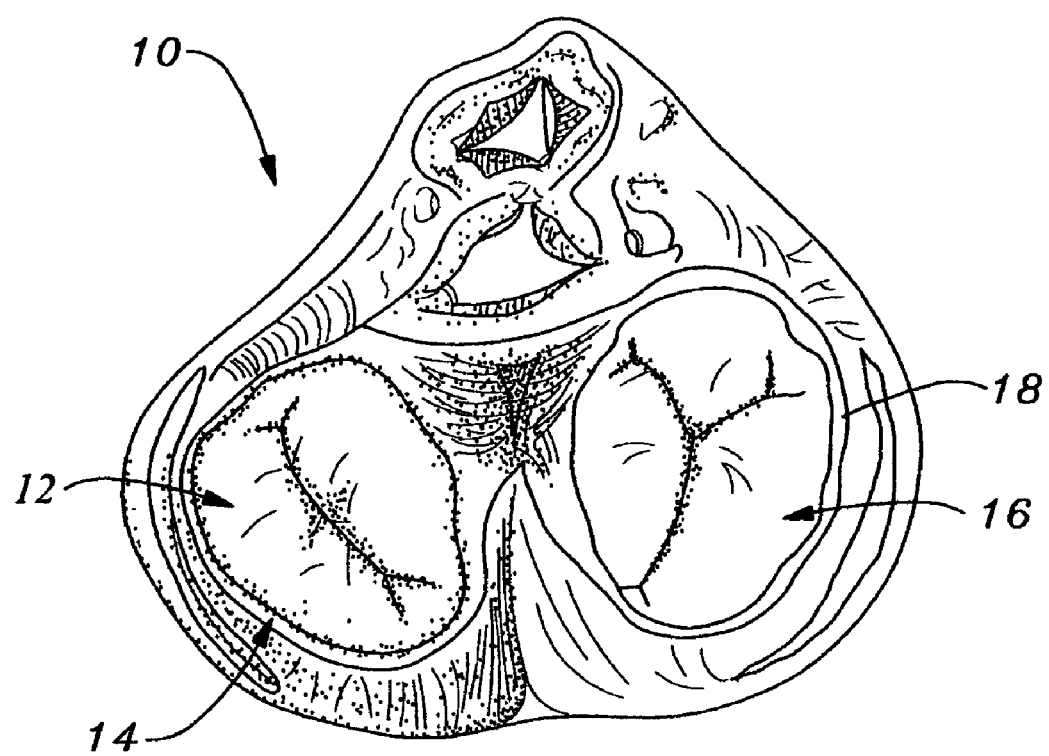
FIG. 1 shows a top sectional view of the mitral and tricuspid valves and valve annuli within a heart.

FIG. 1 shows a cross sectional view of the heart 10 having a bicuspid or mitral valve 12 positioned near the mitral valve annulus 14, and a tricuspid valve 16 positioned near the tricuspid valve annulus 18.

Figure 2A:
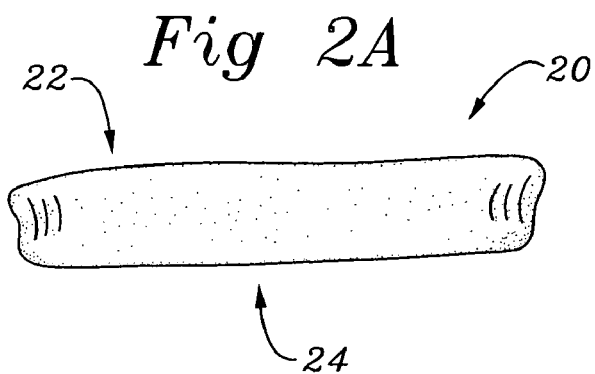
FIG. 2A shows a side view of the annuloplasty ring of the present invention.
Figure 2B:
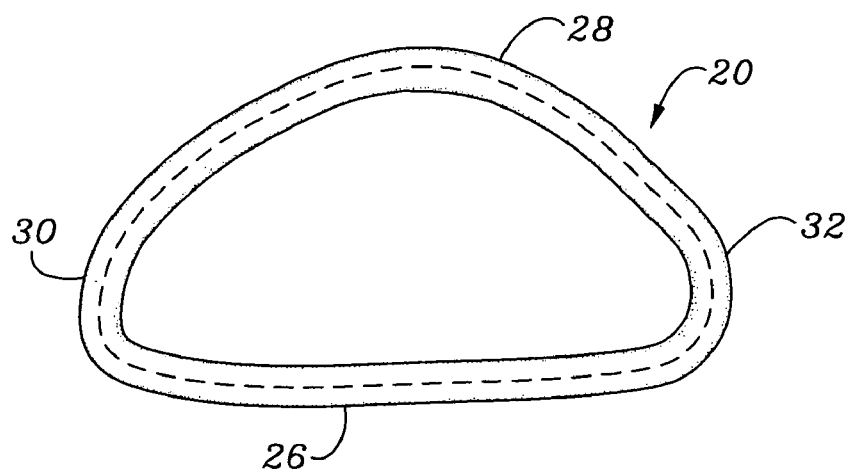
FIG. 2B shows a top view of the annuloplasty ring of the present invention.
Figure 2C:
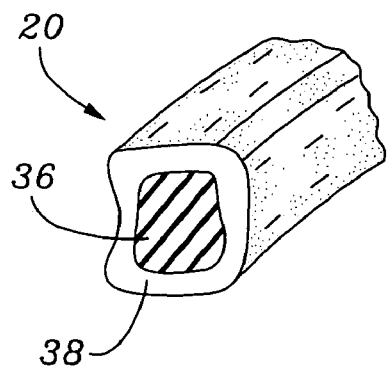
FIG. 2C shows a cross sectional view of the annuloplasty ring of the present invention.

Various views of the present invention are illustrated in FIGS. 2A–2E. As shown in FIG. 2A, the self-molding annulus ring 20 comprises a first planar surface 22 and an opposing second planar surface 24. FIG. 2B shows the annulus ring 20 having a rectilinear segment 26 and an arcuate segment 28 connected by two curved ends 30 and 32, respectively. As illustrated, the preferred annuloplasty ring 20 is generally "D" shaped to conform to the shape of a typical mitral valve annulus. Alternatively, the ring 20 may be manufactured in any shape suitable for implantation about an annulus. For example, the present invention may be manufactured in a generally round or oval shape thereby permitting use of the present invention to remodel an otherwise incompetent tricuspid valve. FIG. 2C shows a cross-sectional view of the annuloplasty ring 20 having an elastic sizing member 36 positioned within an attachment sheath 38. While the cross-sectional view illustrated in FIG. 2C is substantially rectangular, it is to be appreciated that the cross-section can alternatively be of another dimension such as triangular, circular or any dimension that cooperates with the native annulus.

The elastic sizing member 36 preferably comprises a biologically-compatible materials such as, without limitation, elastomer, silicon, or any other material having sufficient resiliency to permit pre-stretching of the annuloplasty ring 20 prior to and during implantation, while having sufficient contractive force to decrease the size of the valve annulus to a desired diameter. The attachment sheath 38 provides a suitable material for suturing or otherwise attaching the annulus ring 20 to the annulus tissue and promoting tissue growth therein. The attachment sheath 38 preferably comprises a biologically-compatible material such as, without limitation, Dacron (polyethylene terepthalate), polyester knit, PTFE knit, and ePTFE knit. The attachment sheath may also be treated with a biologically-compatible tissue growth factor or other medicament to aid in treating the attachment area. Those skilled in the art will appreciate that the present invention reduces or eliminates the occurrence of systolic anterior motion (SAM), wherein the anterior leaflet of the mitral valve bulges into the left ventricular outflow track (LVOT) thereby obstructing blood flow into the aorta.

Figure 2D:
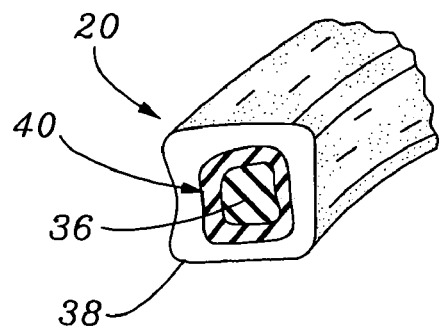
FIG. 2D shows an alternate embodiment of the annuloplasty ring of the present invention having a support member positioned therein.
Figure 2E:
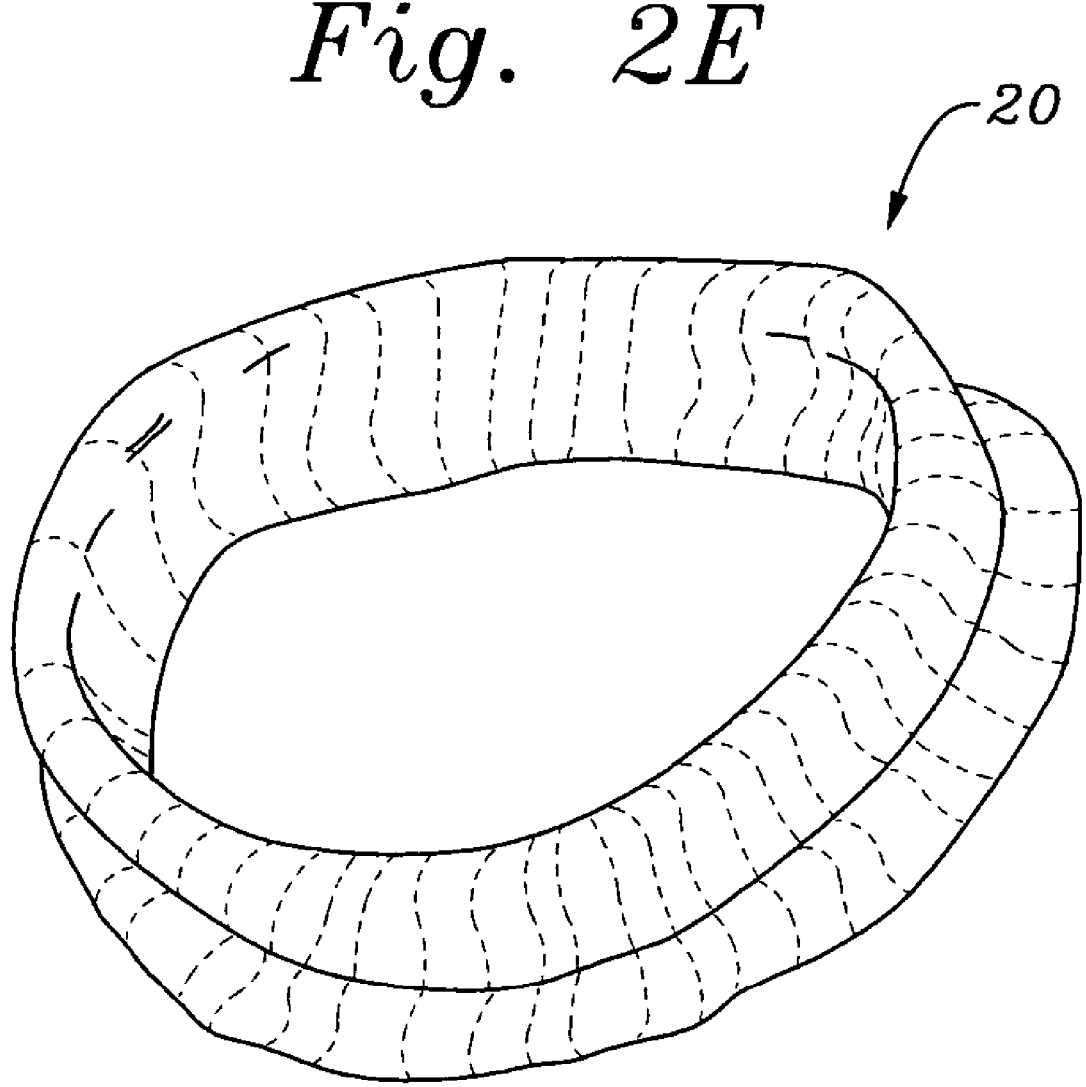
FIG. 2E shows a perspective view of the annuloplasty ring of the present invention.

An alternate embodiment of the present invention is shown in FIG. 2D having support members 40 positioned between the sizing member 36 and the attachment sheath 38. The support members 40 are preferably fabricated from a biologically-compatible materials having a comparable modulus of resiliency such as, without limitation, elastomer, rubber, silicon, or another material having sufficient resiliency to permit pre-stretching prior to implantation while sufficient providing support to the valve annulus. The support member 40 provides additional support of the valve and valve annulus FIG. 2E shows a perspective view of the annuloplasty ring of the present invention.

Figure 3A:
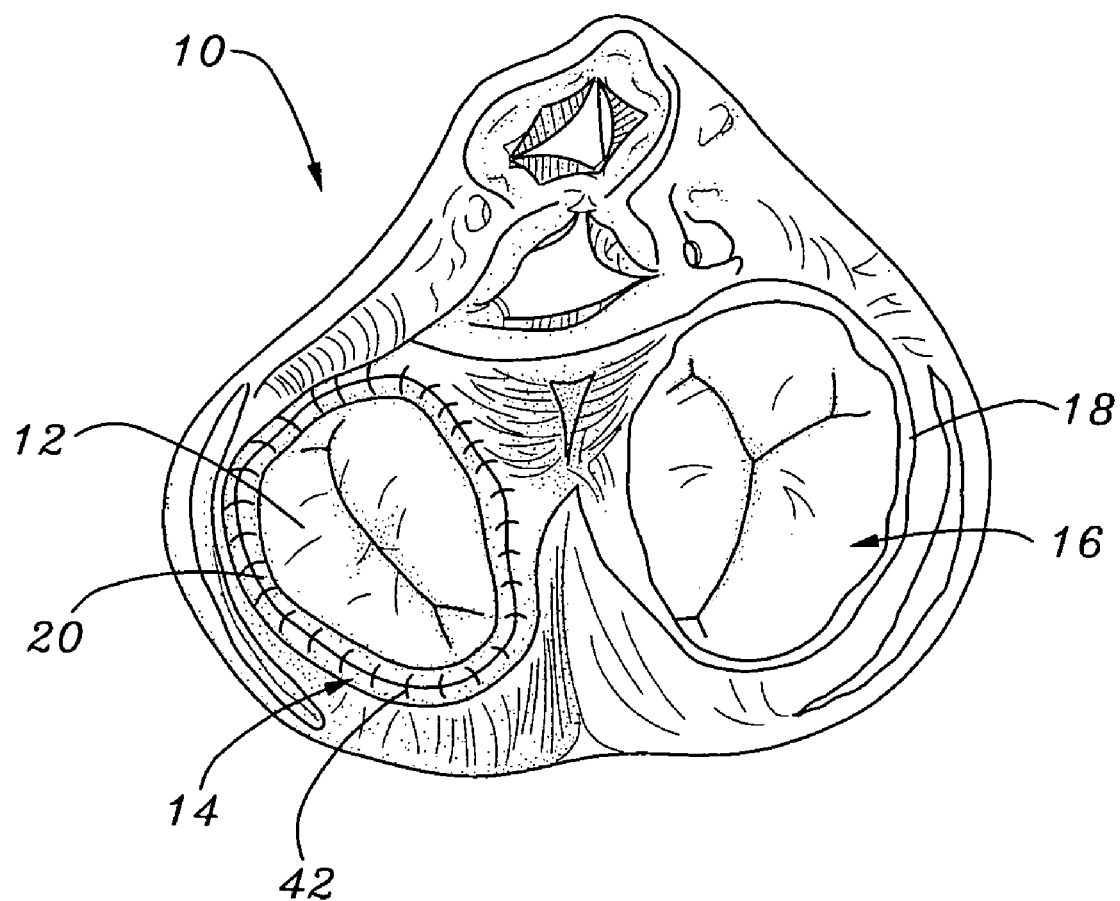
FIG. 3A shows a top sectional view of the annuloplasty ring of the present invention positioned within the valve annulus of the mitral valve.
Figure 3B:
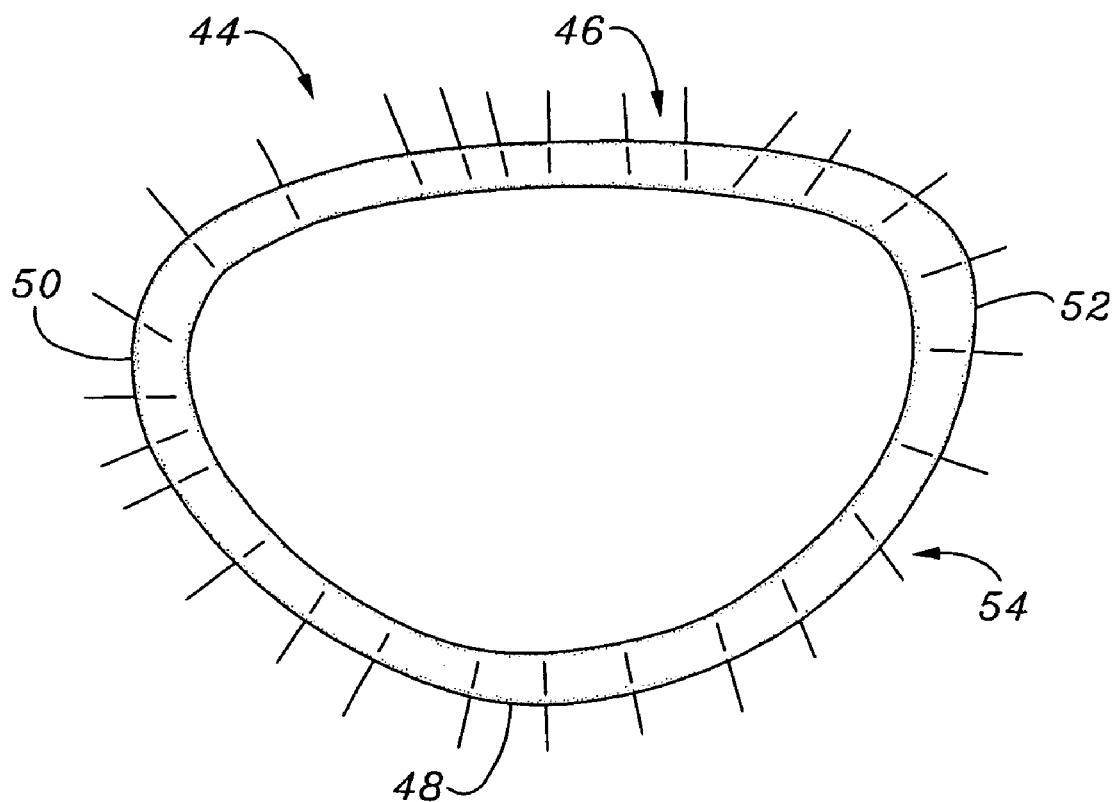
FIG. 3B shows a top view of an embodiment of the present embodiment having a plurality of attachment devices disposed thereon.
Figure 3C:
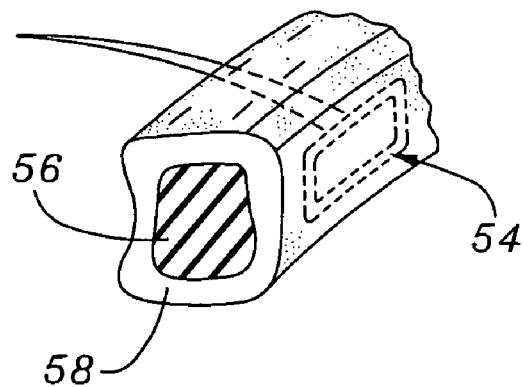
FIG. 3C shows a cross sectional view of the present embodiment with an attachment device disposed thereon.

The annuloplasty ring of the present invention may be attached to the annulus or surrounding tissue using a plurality of devices. Referring to FIG. 3A, the annulus ring 20 may be attached to the valve annulus, either 14 or 18, with sutures 42. FIG. 3B shows an alternate embodiment of the present invention utilizing attachment devices positioned on the annuloplasty ring. Like the previous embodiments, the present embodiment of the ring 44 comprises a rectilinear segment 46 attached to an arcuate portion 48 with two curved ends 50 and 52 positioned therebetween. A number of attachment devices 54 are positioned around the ring 44 to facilitate attachment of the ring 44 to the annulus tissue. FIG. 3C shows the internal materials of the present invention having a sizing member 56 and an tissue-engaging sheath 58 disposed thereon.

Figure 3D:
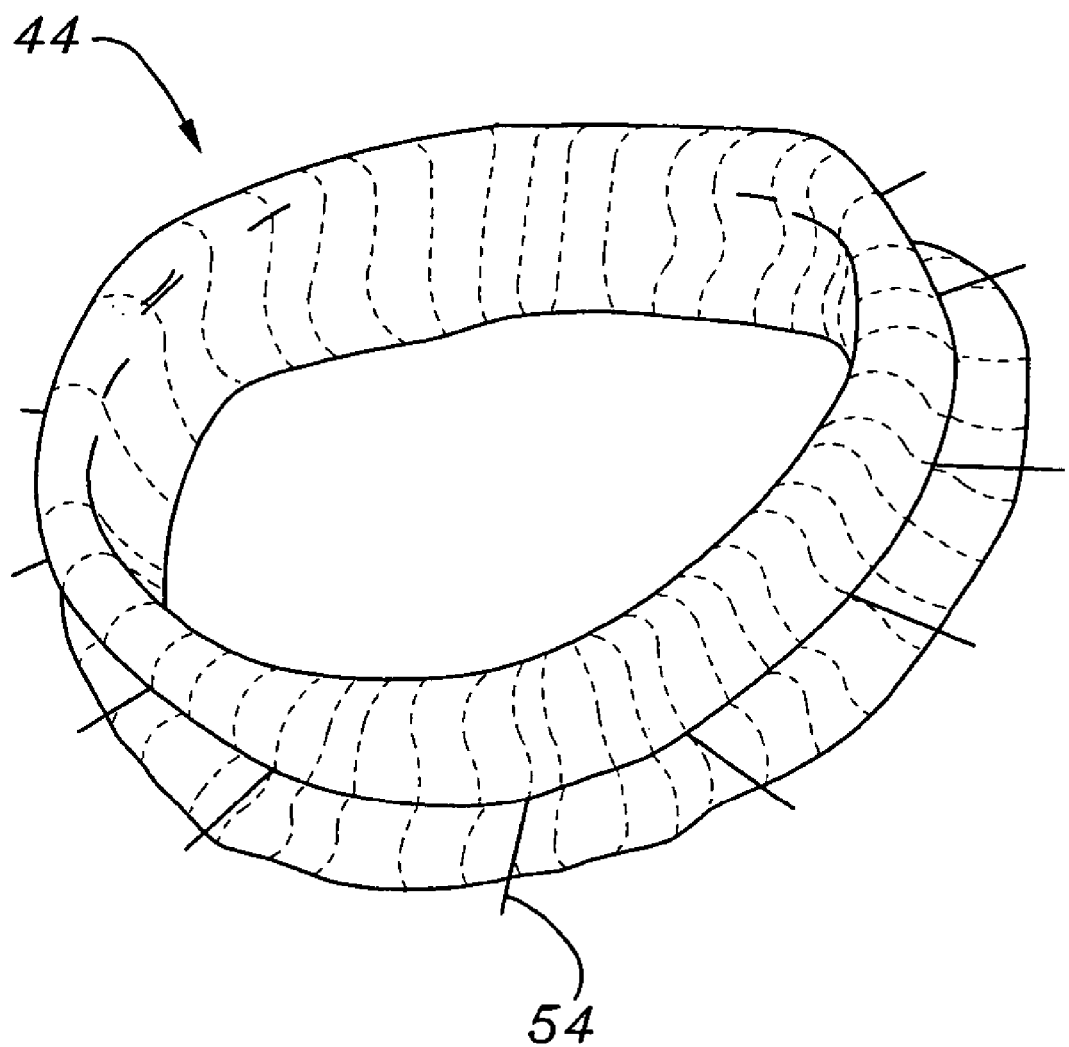
FIG. 3D shows a perspective view of the present embodiment having a plurality of attachment devices disposed thereon.

Like the previous embodiments, the sizing member 56 is preferably manufactured from a biologically-compatible material such as, without limitation, elastotner, silicon, or any other material having sufficient resiliency to permit pre-stretching of the annuloplasty ring 44 prior to and during implantation, while having sufficient coinractive force to decrease the size of the valve annulus to a desired diameter. Similarly, the tissue-engaging sheath 58 is preferably manufactured from a biologically-compatible material having comparable resiliency, such as, without limitation, Dacron (polyethylene terepthalate), polyester knit, PTFE knit, and ePTFE knit, and may further incorporate tissue growth enhancing materials. The attachment device 54 may comprise various tissue-engaging devices, including, for example, needles, barbs, or hooks. Those skilled in the art will appreciate the attachment devices 54 is preferably manufactured from a biologically-compatible material such as, without limitation, stainless steel, titanium, or Nickel-Titanium alloy (Nitinol). FIG. 3D shows a perspective view of the annuloplasty ring of the present embodiment having a plurality of attachment devices 54 positioned about the device body 44.

Figure 4A:
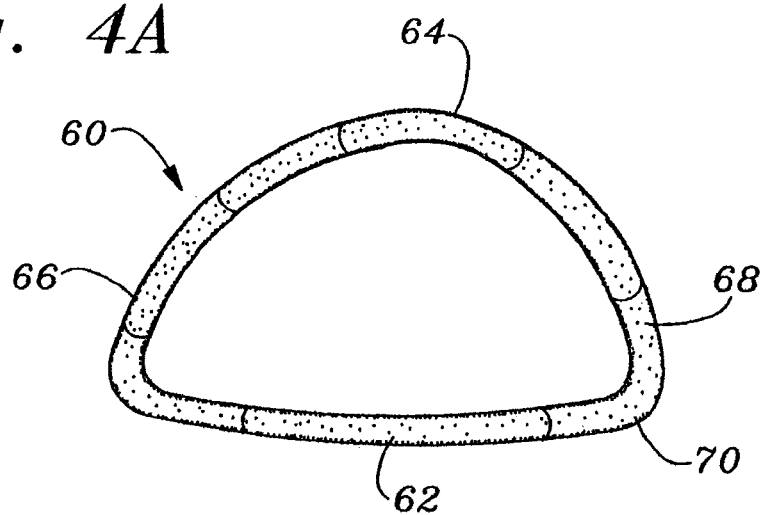
FIG. 4A shows a top view of the present embodiment of the present invention in a contracted state having a plurality of size support members positioned thereon.
Figure 4B:
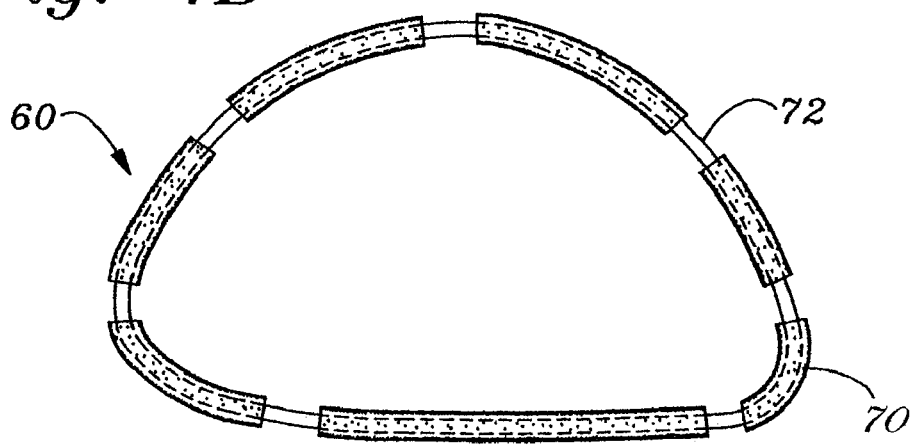
FIG. 4B shows a top view of the present embodiment of the present invention in a stretched state having a plurality of size support members positioned thereon.
Figure 4C:
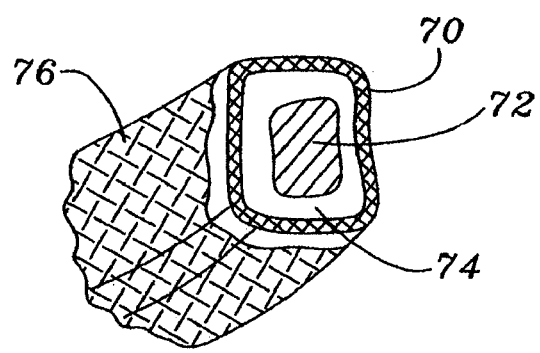
FIG. 4C shows a cross sectional view of the embodiment of FIGS. 4A and 4B.

FIGS. 4A–4C show an alternative embodiment of the present invention which includes size constraining support members. FIG. 4A shows the annuloplasty ring 60 of the present embodiment in a contracted state, wherein the ring 60 comprises a rectilinear segment 62, an arcuate segment 64, and two curved ends 66 and 68 positioned therebetween. The ring 60 is comprised of a series of support members 70 positioned about the device. The support members 70 are positioned immediately adjacent to each other in the contracted state, though it is to be understood that the resilient inner sizing member is biased toward a fully relaxed diameter that is smaller than the diameter in the contracted state. In other words, the plurality of support members 70 constrain contraction of the inner sizing member 72 to a contracted diameter that is larger than the fully relaxed diameter. FIG. 4B shows the ring 60 stretched prior to implantation, having the resilient inner sizing member 72 positioned within the support members 70. As shown in FIG. 4C, each support member 70 has a receiving lumen 74 formed therein which is capable of receiving the inner sizing member 72. The attachment sheath 76 may be positioned on the exterior of the support members 70. Prior to implantation, the ring 60 is pre-stretched to a fully expanded diameter roughly equivalent to the diameter of the dilated valve annulus and the attachment sheath is attached to the tissue using, for example, sutures, staples, or barbs. Once the ring 60 is suitably positioned with the valve annulus and attached thereto, the insertion device (not shown) is removed and the ring 60 contracts causing each size support member 70 to engage the adjacent support members 70, thereby limiting the degree of contraction that the ring 60 may achieve. Again, the plurality of support members 70 constrain contraction of the inner sizing member 72 to a contracted diameter that is smaller than the fully expanded diameter but larger than the fully relaxed diameter.

The support members 70 are preferably manufactured from a biologically-compatible material such as, without limitation, stainless steel, titanium, or plastic. Like the previous embodiment, the inner sizing member 72 is preferably manufactured from a biologically compatible material such as, without limitation, elastomer, silicon, or any other material having sufficient resiliency to permit pre-stretching of the annuloplasty ring 60 prior to and during implantation, while having sufficient contractive force to decrease the size of the valve annulus to a desired diameter. Similarly, the attachment sheath 76 is preferably manufactured from a resilient biologically-compatible material such as, without limitation, Dacron (polyethylene terephthalate), polyester knit, PTFE knit, and ePTFE knit, or may incorporate tissue growth-enhancing materials.

The present invention further discloses a method of repairing a dilated or otherwise incompetent annulus. An exemplary open-chest surgical repair of a mitral valve will be disclosed herein. It should be understood the method disclosed herein is not intended to limit the scope of the present invention in any way.

The mitral valve partially forms the atrio-ventricular junction between the left atrium and left ventricle of the heart and is most easily reached through the wall of the left atrium. Those skilled in the art will appreciate that the wall of the left atrium is may be accessed through a medial sternotomy procedure. To gain access to the mitral valve during the sternotomy, the surgeon rotates the heart to an anterior position, thereby providing access to the left atrium. An incision is made in the left atrium, thereby providing access to the mitral valve and the valve annulus.

To insert the annuloplasty ring of the present invention, the ring 20 is stretched for positioning on an insertion device. Those skilled in art will appreciate the present invention may be inserted on a plurality of insertion devices know in the art. Additionally, the annuloplasty ring may be positioned on the insertion device at the time of manufacture or immediately prior to implantation. Ideally, the annuloplasty ring should be stretched to a size commensurate with the diameter of the dilated valve annulus. The ring, positioned on the insertion device, is positioned proximate to the valve annulus and attached to surrounding tissue in a plurality of known and accepted manners, including, suturing, stapling, or any other biologically-compatible attachment technique. With the ring sufficiently attached, the insertion device is removed, resulting in the annuloplasty ring contracting to its pre-stretched diameter, thereby rendering the valve competent. Those skilled in the art will appreciate the contractive force of the annuloplasty ring will determine the amount of post-implantation valvular dilation, thereby permitting the surgeon to accurately predict the post-implantation valve diameter.

While the foregoing describes the preferred embodiments of the invention, various alternatives, modifications, and equivalents may be used. By way of example but not of limitation, alternative insertion devices, and alternative attachment devices may be used. It will thus be obvious that certain other modifications may be practiced within the scope of the appended claims.

What is claimed is:

1. A method of implanting an annuloplasty ring in a heart valve annulus, comprising:
   providing a resilient annuloplasty ring having a contracted diameter;
   stretching the annuloplasty ring to an expanded diameter commensurate with the diameter of a dilated heart valve annulus;
   positioning the annuloplasty ring within the heart valve annulus;
   maintaining the annuloplasty ring at its expanded diameter while attaching the annuloplasty ring to the dilated heart valve annulus by using an attachment device to physically connect the annuloplasty ring to the annulus; and
   permitting the annuloplasty ring in contract inward from its expanded diameter so as to decrease the size of the attached heart valve annulus.

2. The method of claim 1, wherein the resilient annuloplasty ring comprises a resilient inner sizing member and an outer attachment sheath enclosing the sizing member.

3. The method of claim 2, wherein the attachment device comprises a plurality of members positioned on the annuloplasty ring.

4. The method of claim 3, wherein the plurality of members is selected from the group consisting of:
   needles,
   barbs, and
   hooks.

5. The method of claim 3, wherein the material of the plurality of members is selected from the group consisting of:
  stainless steel,
  titanium, and
  a nickel-titanium alloy.

6. The method of claim 2, wherein the attachment device comprises at least one suture, and wherein the step of attaching the annuloplasty ring to the dilated heart valve annulus comprises passing the suture through the attachment sheath and through the heart valve annulus.

7. The method of claim 2, wherein said outer attachment sheath is selected from the group consisting of:
  biologically compatible fabric mesh,
  polyethylene terephthalate,
  polyester knit,
  PTFE knit, and
  ePTFE knit.

8. The method of claim 2, wherein said outer attachment sheath comprises a medicament to induce tissue growth.

9. The method of claim 1, wherein the annuloplasty ring further includes a resilient sizing member having a relaxed diameter, and wherein the method further comprises limiting contraction of the annuloplasty ring to a contracted diameter that is larger than the relaxed diameter of the resilient sizing member.

10. The method of claim 9, wherein the annuloplasty ring includes a series of support members positioned on the sizing member, and wherein the step of limiting contraction is accomplished by engagement of the support members with one another.

11. The method of claim 10, wherein each support member comprises a body member having a lumen formed therein, said lumen being capable of receiving the sizing member therein.

12. The method of claim 2, wherein said resilient sizing member comprises a biologically compatible elastomer.

13. The method of claim 1, wherein the step of maintaining the annuloplasty ring at its expanded diameter comprises positioning the annuloplasty ring on an insertion device.

14. The method of claim 13, wherein the annuloplasty ring is positioned on the insertion device at the time of manufacture.

15. The method of claim 13, wherein the annuloplasty ring is positioned on the insertion device immediately prior to implantation.

16. A method of implanting a self-molding annuloplasty ring in a heart valve annulus, comprising:
  providing a resilient annuloplasty ring having a contracted diameter, the annuloplasty ring including a resilient inner sizing member having a relaxed diameter and an outer attachment sheath;
  stretching the annuloplasty ring to an expanded diameter commensurate with the diameter of a dilated heart valve annulus;
  positioning the expanded annuloplasty ring on an insertion device;
  delivering the insertion device and expanded annuloplasty ring to the dilated heart valve annulus;
  positioning the annuloplasty ring within the heart valve annulus;
  attaching the annuloplasty ring to the dilated heart valve annulus by using an attachment device to physically connect the attachment sheath to the annulus; and
  removing the insertion device so as to permit the annuloplasty ring to contract inward from its expanded diameter and decrease the size of the attached heart valve annulus.

17. The method of claim 16, wherein the attachment device comprises a plurality of members positioned on the annuloplasty ring.

18. The method of claim 17, wherein the plurality of members is selected from the group consisting of:
  needles
  barbs, and
  hooks.

19. The method of claim 17, wherein the material of the plurality of members is selected from the group consisting of:
  stainless steel,
  titanium, and
  a nickel-titanium alloy.

20. The method of claim 16, wherein the attachment device comprises at least one suture, and wherein the step of attaching the annuloplasty ring to the dilated heart valve annulus comprises passing the suture through the attachment sheath and through the heart valve annulus.

21. The method of claim 16, wherein said outer attachment sheath is selected from the group consisting of:
  biologically compatible fabric mesh,
  polyethylene terephthalate,
  polyester knit,
  PTFE knit, and
  ePTFE knit.

22. The method of claim 16, wherein said outer attachment sheath comprises a medicament to induce tissue growth.

23. The method of claim 16, wherein the method further comprises limiting contraction of the annuloplasty ring to a contracted diameter that is larger than the relaxed diameter of the inner sizing member.

24. The method of claim 23, wherein the annuloplasty ring further includes a series of support members positioned on the inner sizing member, and wherein the step of limiting contraction is accomplished by engagement of the support members with one another.

25. The method of claim 24, wherein each support member comprises a body member having a lumen formed therein, said lumen being capable of receiving the sizing member therein.

26. The method of claim 16, wherein said resilient inner sizing member comprises a biologically compatible elastomer.

27. The method of claim 16, wherein the annuloplasty ring is positioned on the insertion device at the time of manufacture.

28. The method of claim 16, wherein the annuloplasty ring is positioned on the insertion device immediately prior to implantation.

29. A method of implanting an annuloplasty ring in a heart valve annulus, comprising:
  providing a resilient annuloplasty ring having a contracted diameter and a resilient sizing member having a relaxed diameter;
  stretching the annuloplasty ring to an expanded diameter commensurate with the diameter of a dilated heart valve annulus;
  positioning the annuloplasty ring within the heart valve annulus;

maintaining the annuloplasty ring at its expanded diameter while attaching the annuloplasty ring to the dilated heart valve annulus;
permitting the annuloplasty ring to contract inward from its expanded diameter so as to decrease the size of the attached heart valve annulus; and
limiting contraction of the annuloplasty ring to a contracted diameter that is larger than the relaxed diameter of the sizing member.

30. The method of claim 29, wherein the annuloplasty ring includes a series of support members positioned on the sizing member, and wherein the step of limiting contraction is accomplished by engagement of the support members with one another.

31. The method of claim 30, wherein each support member comprises a body member having a lumen formed therein, said lumen being capable of receiving the sizing member therein.

32. A method of implanting an annuloplasty ring in a heart valve annulus, comprising:
providing a resilient annuloplasty ring having a contracted diameter;
stretching the annuloplasty ring to an expanded diameter commensurate with the diameter of a dilated heart valve annulus;
positioning the annuloplasty ring within the heart valve annulus;
maintaining the annuloplasty ring at its expanded diameter while attaching the annuloplasty ring to the dilated heart valve annulus, wherein the annuloplasty ring is maintained at its expanded diameter by positioning the annuloplasty ring on an insertion device at the time of manufacture; and
permitting the annuloplasty ring to contract inward from its expanded diameter so as to decrease the size of the attached heart valve annulus.

33. A method of implanting an annuloplasty ring in a heart valve annulus, comprising:
providing a resilient annuloplasty ring having a contracted diameter;
stretching the annuloplasty ring to an expanded diameter commensurate with the diameter of a dilated heart valve annulus;
positioning the annuloplasty ring within the heart valve annulus;
maintaining the annuloplasty ring at its expanded diameter while attaching the annuloplasty ring to the dilated heart valve annulus, wherein the annuloplasty ring is maintained at its expanded diameter by positioning the annuloplasty ring on an insertion device immediately prior to implantation; and
permitting the annuloplasty ring to contract inward from its expanded diameter so as to decrease the size of the attached heart valve annulus.

34. A method of implanting a self-molding annuloplasty ring in a heart valve annulus, comprising:
providing a resilient annuloplasty ring having a contracted diameter, the annuloplasty ring including a resilient inner sizing member and an outer attachment sheath, wherein said outer attachment sheath is selected from the group consisting of:
biologically compatible fabric mesh,
polyethylene terephthalate,
polyester knit,
PTFE knit, and
ePTFE knit;
stretching the annuloplasty ring to an expanded diameter commensurate with the diameter of a dilated heart valve annulus;
positioning the expanded annuloplasty ring on an insertion device;
delivering the insertion device and expanded annuloplasty ring to the dilated heart valve annulus;
positioning the annuloplasty ring within the heart valve annulus;
attaching the annuloplasty ring to the dilated heart valve annulus; and
removing the insertion device so as to permit the annuloplasty ring to contract inward from its expanded diameter and decrease the size of the attached heart valve annulus.

35. A method of implanting a self-molding annuloplasty ring in a heart valve annulus, comprising:
providing a resilient annuloplasty ring having a contracted diameter, the annuloplasty ring including a resilient inner sizing member and an outer attachment sheath, wherein said outer attachment sheath comprises a medicament to induce tissue growth;
stretching the annuloplasty ring to an expanded diameter commensurate with the diameter of a dilated heart valve annulus;
positioning the expanded annuloplasty ring on an insertion device;
delivering the insertion device and expanded annuloplasty ring to the dilated heart valve annulus;
positioning the annuloplasty ring within the heart valve annulus;
attaching the annuloplasty ring to the dilated heart valve annulus; and
removing the insertion device so as to permit the annuloplasty ring to contract inward from its expanded diameter and decrease the size of the attached heart valve annulus.

36. A method of implanting a self-molding annuloplasty ring in a heart valve annulus, comprising:
providing a resilient annuloplasty ring having a contracted diameter, the annuloplasty ring including a resilient inner sizing member having a relaxed diameter and an outer attachment sheath;
stretching the annuloplasty ring to an expanded diameter commensurate with the diameter of a dilated heart valve annulus;
positioning the expanded annuloplasty ring on an insertion device;
delivering the insertion device and expanded annuloplasty ring to the dilated heart valve annulus;
positioning the annuloplasty ring within the heart valve annulus;
attaching the annuloplasty ring to the dilated heart valve annulus;
removing the insertion device so as to permit the annuloplasty ring to contract inward from its expanded diameter and decrease the size of the attached heart valve annulus; and
limiting contraction of the annuloplasty ring to a contracted diameter that is larger than the relaxed diameter of the inner sizing member.

37. The method of claim 36, wherein the annuloplasty ring further includes a series of support members positioned on the inner sizing member, and wherein the step of limiting contraction is accomplished by engagement of the support members with one another.

38. The method of claim 37, wherein each support member comprises a body member having a lumen formed therein, said lumen being capable of receiving the sizing member therein.

39. A method of implanting a self-molding annuloplasty ring in a heart valve annulus, comprising:
   providing a resilient annuloplasty ring having a contracted diameter, the annuloplasty ring including a resilient inner sizing member comprising a biologically compatible elastomer and an outer attachment sheath;
   stretching the annuloplasty ring to an expanded diameter commensurate with the diameter of a dilated heart valve annulus;
   positioning the expanded annuloplasty ring on an insertion device;
   delivering the insertion device and expanded annuloplasty ring to the dilated heart valve annulus;
   positioning the annuloplasty ring within the heart valve annulus;
   attaching the annuloplasty ring to the dilated heart valve annulus; and
   removing the insertion device so as to permit the annuloplasty ring to contract inward from its expanded diameter and decrease the size of the attached heart valve annulus.

40. A method of implanting a self-molding annuloplasty ring in a heart valve annulus, comprising:
   providing a resilient annuloplasty ring having a contracted diameter, the annuloplasty ring including a resilient inner sizing member and an outer attachment sheath;
   stretching the annuloplasty ring to an expanded diameter commensurate with the diameter of a dilated heart valve annulus;
   positioning the expanded annuloplasty ring on an insertion device at the time of manufacture;
   delivering the insertion device and expanded annuloplasty ring to the dilated heart valve annulus;
   positioning the annuloplasty ring within the heart valve annulus;
   attaching the annuloplasty ring to the dilated heart valve annulus; and
   removing the insertion device so as to permit the annuloplasty ring to contract inward from its expanded diameter and decrease the size of the attached heart valve annulus.

41. A method of implanting a self-molding annuloplasty ring in a heart valve annulus, comprising:
   providing a resilient annuloplasty ring having a contracted diameter, the annuloplasty ring including a resilient inner sizing member and an outer attachment sheath;
   stretching the annuloplasty ring to an expanded diameter commensurate with the diameter of a dilated heart valve annulus;
   positioning the expanded annuloplasty ring on an insertion device immediately prior to implantation;
   delivering the insertion device and expanded annuloplasty ring to the dilated heart valve annulus;
   positioning the annuloplasty ring within the heart valve annulus;
   attaching the annuloplasty ring to the dilated heart valve annulus; and
   removing the insertion device so as to permit the annuloplasty ring to contract inward from its expanded diameter and decrease the size of the attached heart valve annulus.

* * * * *